(12) United States Patent
Chono

(10) Patent No.: US 11,497,474 B2
(45) Date of Patent: Nov. 15, 2022

(54) ULTRASOUND DIAGNOSIS DEVICE

(71) Applicant: HITACHI, LTD., Tokyo (JP)

(72) Inventor: Tomoaki Chono, Tokyo (JP)

(73) Assignee: FUJIFILM Healthcare Corporation, Kashiwa (JP)

(*) Notice: Subject to any disclaimer, the term of this patent is extended or adjusted under 35 U.S.C. 154(b) by 528 days.

(21) Appl. No.: 16/610,977

(22) PCT Filed: Mar. 23, 2018

(86) PCT No.: PCT/JP2018/011594
§ 371 (c)(1),
(2) Date: Nov. 5, 2019

(87) PCT Pub. No.: WO2018/207474
PCT Pub. Date: Nov. 15, 2018

(65) Prior Publication Data
US 2020/0060656 A1 Feb. 27, 2020

(30) Foreign Application Priority Data

May 8, 2017 (JP) .............................. JP2017-092099

(51) Int. Cl.
*A61B 8/08* (2006.01)
*A61B 8/06* (2006.01)
*A61B 8/00* (2006.01)

(52) U.S. Cl.
CPC ................ *A61B 8/488* (2013.01); *A61B 8/06* (2013.01); *A61B 8/463* (2013.01)

(58) Field of Classification Search
CPC ........... A61B 8/488; A61B 8/06; A61B 8/463; A61B 8/065; A61B 8/0883; A61B 8/0891;
(Continued)

(56) References Cited

U.S. PATENT DOCUMENTS 8,295,569 B2 10/2012 Park
2006/0052704 A1 3/2006 Baba
(Continued)

FOREIGN PATENT DOCUMENTS

JP H3-210248 A 9/1991
JP H7-241289 9/1995
(Continued)

OTHER PUBLICATIONS

International Preliminary Report on Patentability issued in International Application No. PCT/JP2018/011594 and Notification of Transmittal of Copy thereof dated Nov. 21, 2019.
(Continued)

*Primary Examiner* — Jonathan Cwern
(74) *Attorney, Agent, or Firm* — Foley & Lardner LLP

(57) ABSTRACT

A Doppler waveform generation unit 30 obtains Doppler information from a reception signal collected from a diagnosis region and generates a Doppler waveform. An initial time-phase setting unit 40 sets a beginning initial time-phase and an ending initial time-phase of the Doppler waveform. In the setting, an electrocardiographic waveform signal obtained from a subject using an electrocardiograph or the like and learned data stored in a learned data storage unit 60 are used. A measurement time-phase search unit 50 searches for a beginning time-phase of the Doppler waveform near the beginning initial time-phase, and searches for an ending time-phase of the Doppler waveform near the ending initial time-phase. In the search process, the learned data stored in the learned data storage unit 60 is used.

3 Claims, 6 Drawing Sheets

(58) Field of Classification Search
CPC ..... A61B 8/469; A61B 8/5207; A61B 8/5223; A61B 8/5246; A61B 8/5284; G16H 50/30
See application file for complete search history.

(56) References Cited

U.S. PATENT DOCUMENTS

2015/0223781 A1   8/2015  Abe
2018/0153514 A1*  6/2018  Zhai ................... A61B 5/02444

FOREIGN PATENT DOCUMENTS

| | | |
|---|---|---|
| JP | H7-241290 | 9/1995 |
| JP | H7-241291 | 9/1995 |
| JP | H7-303641 | 11/1995 |
| JP | 2006-102489 | 4/2006 |
| JP | 2014-73272 A | 4/2014 |
| JP | 2015-8775 A | 1/2015 |

OTHER PUBLICATIONS

International Search Report with English translation and Written Opinion issued in corresponding application No. PCT/JP2018/011594 dated Jun. 26, 2018.

* cited by examiner

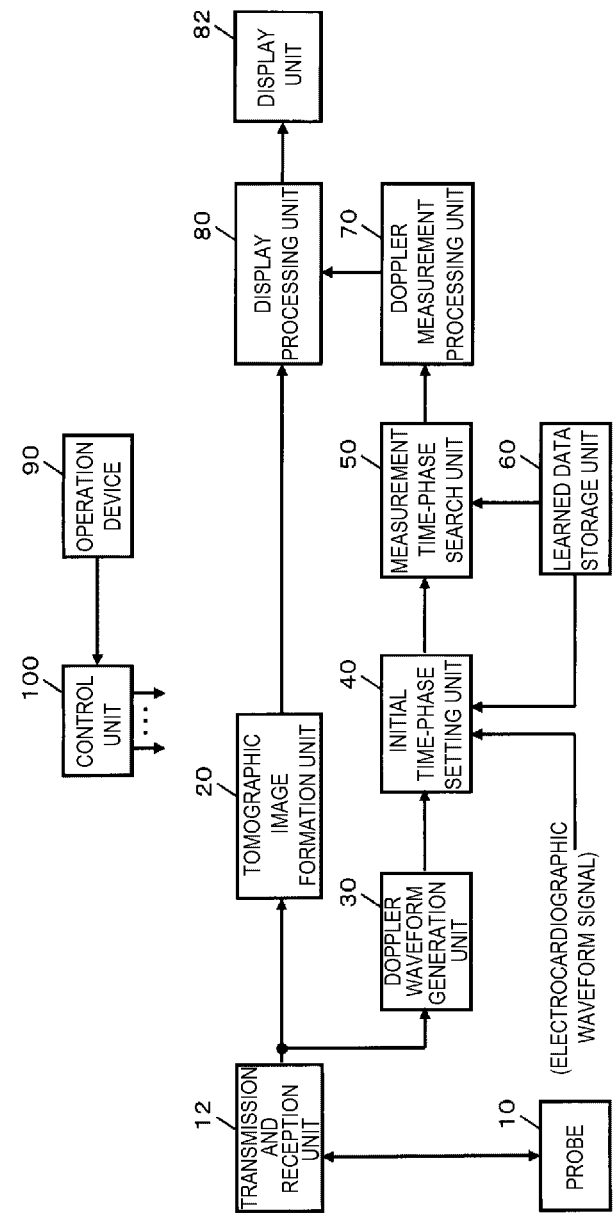
[FIG. 1]

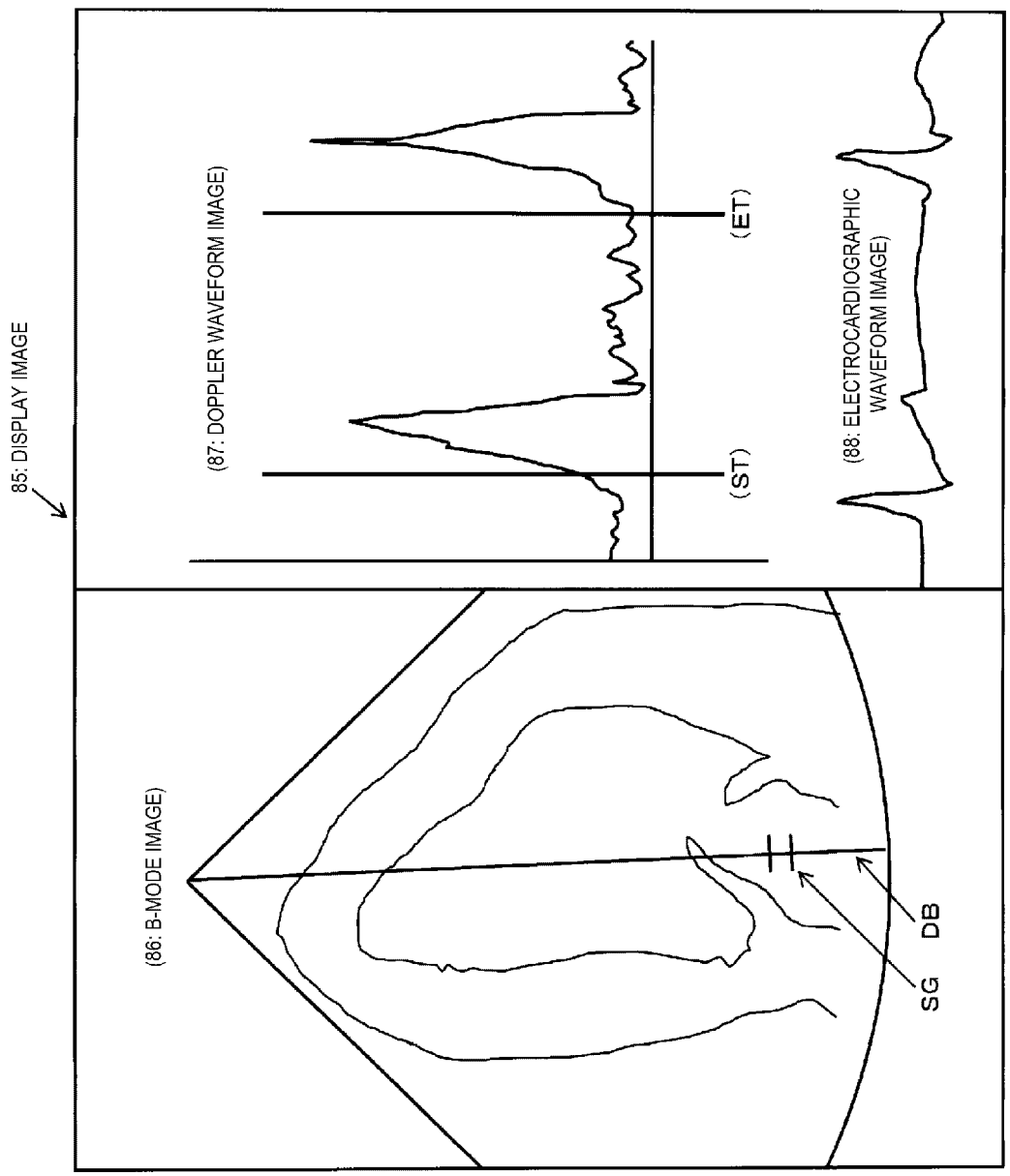
[FIG. 2]

[FIG. 3]
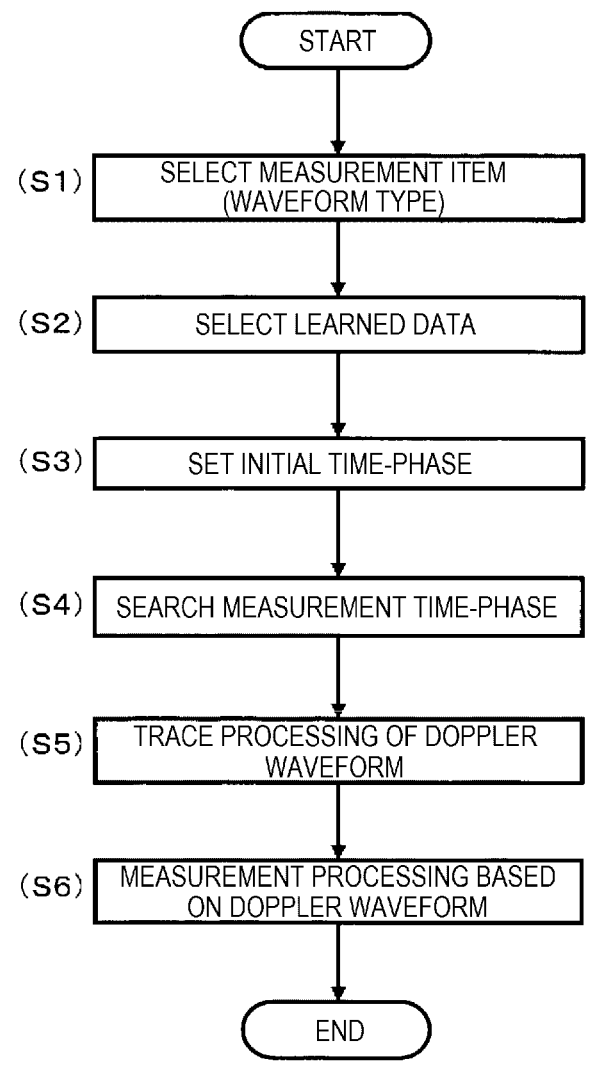

[FIG. 4]

<INITIAL TIME-PHASE DATA>

| MEASUREMENT ITEM (WAVEFORM TYPE) | DISTANCE FROM R (MAIN) (NUMBER OF PIXELS) | | NORMALIZED DISTANCE FROM R (MAIN) | |
|---|---|---|---|---|
| | START | END | START | END |
| MEASUREMENT ITEM 1 | -150 | 50 | -0.5 | 0.1 |
| MEASUREMENT ITEM 2 | 50 | 100 | 0.1 | 0.4 |
| MEASUREMENT ITEM 3 | 50 | 150 | 0.1 | 0.4 |
| MEASUREMENT ITEM 4 | -150 | 50 | -0.5 | 0.1 |
| MEASUREMENT ITEM 5 | -100 | 50 | -0.5 | 0.1 |
| MEASUREMENT ITEM 6 | 50 | 150 | 0.1 | 0.5 |
| MEASUREMENT ITEM 7 | 50 | 150 | 0.1 | 0.5 |
| MEASUREMENT ITEM 8 | 50 | 100 | 0.1 | 0.5 |
| MEASUREMENT ITEM 9 | -200 | 50 | -0.5 | 0.1 |
| MEASUREMENT ITEM 10 | -150 | 50 | -0.5 | 0.1 |

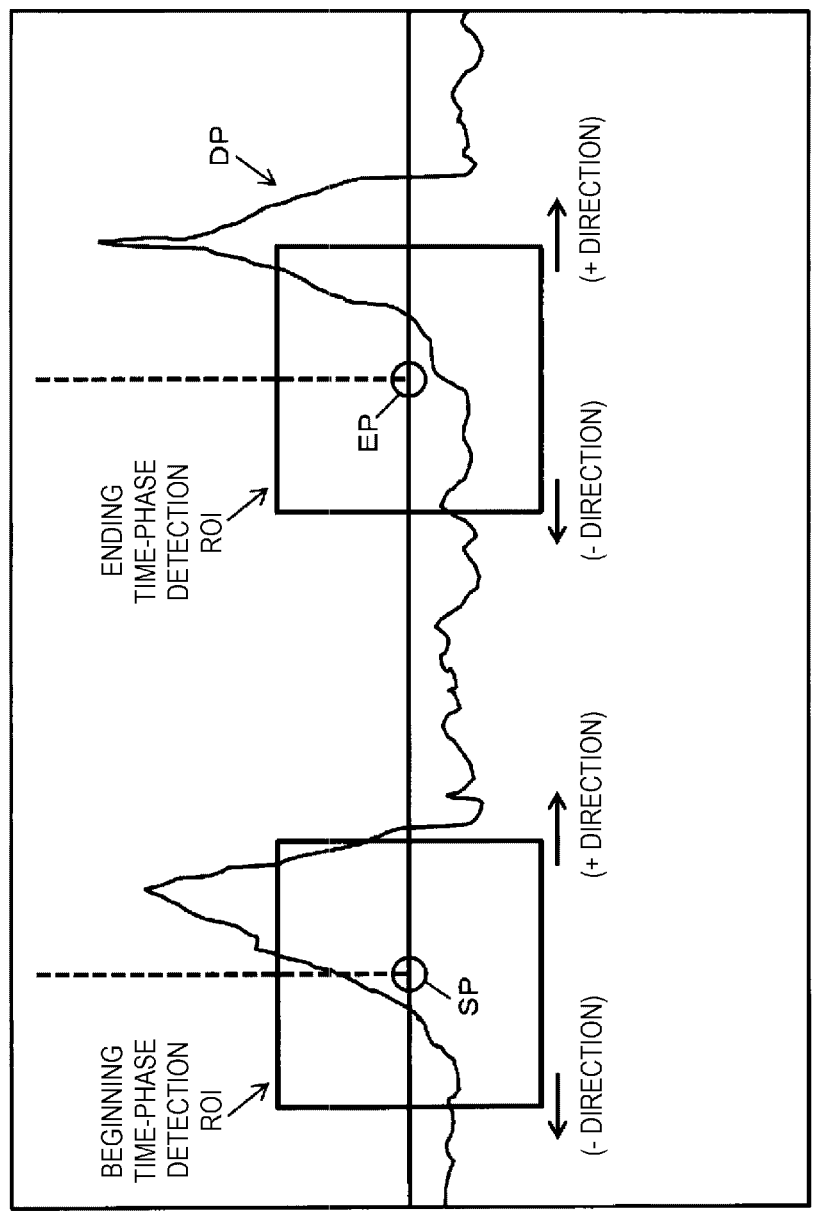

[FIG. 6]
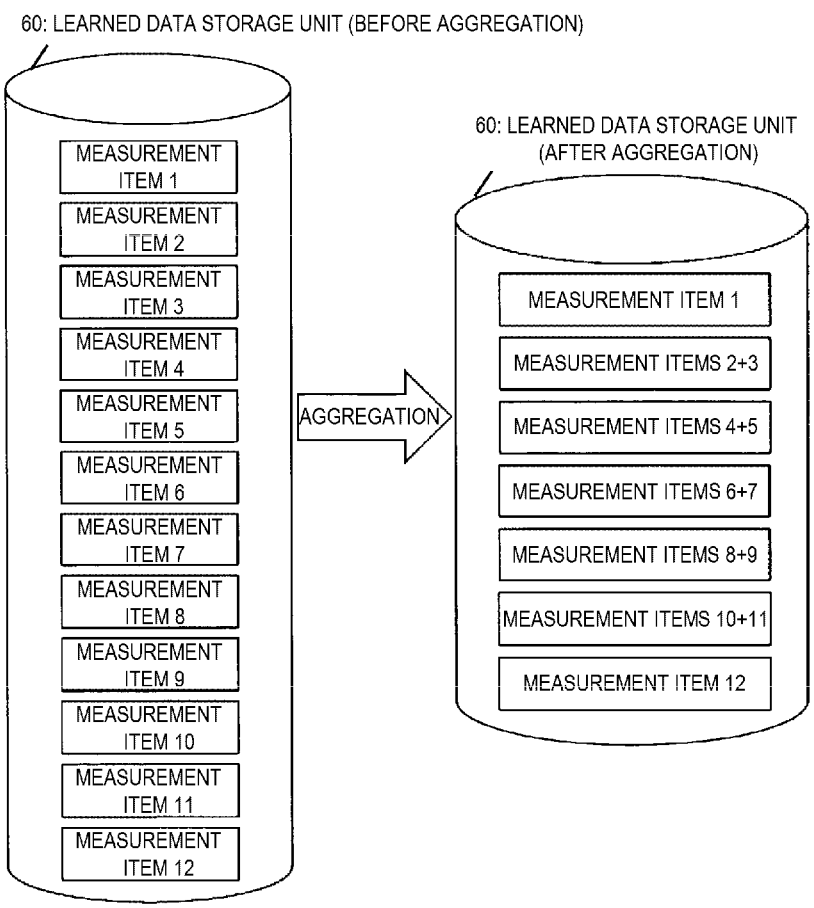

ULTRASOUND DIAGNOSIS DEVICE

TECHNICAL FIELD

The present invention relates to an ultrasound diagnosis device, and particularly to a device for generating a Doppler waveform.

BACKGROUND ART

An ultrasound diagnosis device is a device that forms and displays an ultrasonic image based on reception data obtained by transmitting and receiving ultrasonic waves. For example, a B-mode image is well known as the ultrasonic image. Further, a device is also known to generate a Doppler waveform by obtaining Doppler information from a blood flow, a tissue, or the like in a living body based on reception data obtained by transmitting and receiving ultrasonic waves.

For example, Patent Literature 1 discloses a technique for automatically detecting a beginning position (beginning time-phase) and an ending position (ending time-phase) for measurement in a Doppler waveform of an ultrasonic wave. In addition, Patent Literature 2 discloses a technique of searching for a peak position of a trace waveform (Doppler waveform) using an electrocardiogram waveform (ECG waveform). In addition, for example, Patent Literatures 3 to 6 disclose inventions relating to automatic trace (Doppler auto-trace) of Doppler waveforms.

PRIOR ART LITERATURE

Patent Literature

PTL 1: U.S. Pat. No. 8,295,569 specification
PTL 2: JP-A-2006-102489
PTL 3: JP-A-H7-241289
PTL 4: JP-A-H7-241290
PTL 5: JP-A-H7-241291
PTL 6: JP-A-H7-303641

SUMMARY OF INVENTION

Technical Problem

The Doppler waveform is used for diagnosis related to various tissues such as a heart and a blood vessel, and a large number of measurement items using the Doppler waveform are known. Since a shape of the Doppler waveform and a waveform part used for measurement are different depending on the measurement items, it is not easy to appropriately search for a beginning time-phase and an ending time-phase for measurement in the measurement using the Doppler waveform.

An object of the invention is to provide an improved technique for searching for a beginning time-phase and an ending time-phase of a Doppler waveform.

Solution to Problem

An ultrasound diagnosis device suitable as an aspect of the invention includes: an generating unit that is configured to generate a Doppler waveform based on reception data obtained by transmitting and receiving ultrasonic waves; a storage unit that is configured to store learned data including initial time-phase information statistically obtained from Doppler waveform information for learning; a setting unit that is configured to set a beginning initial time-phase and an ending initial time-phase of a Doppler waveform based on the initial time-phase information; and a search unit that is configured to search for a beginning time-phase of a Doppler waveform near the beginning initial time-phase, and search for an ending time-phase of the Doppler waveform near the ending initial time-phase. According to the aspect, it is possible to search for a range that is defined near the beginning initial time-phase and the ending initial time-phase in search of the beginning time-phase and the ending time-phase of the Doppler waveform.

For example, it is desirable that the storage unit stores, as the initial time-phase information, a start distance corresponding to time from a characteristic time-phase of an electrocardiographic waveform to the beginning initial time-phase, and an end distance corresponding to time from the characteristic time-phase of the electrocardiographic waveform to the ending initial time-phase, and the setting unit sets a time-phase separated by the start distance from the characteristic time-phase of the electrocardiographic waveform obtained from the subject to be diagnosed as the beginning initial time-phase of the Doppler waveform of the subject to be diagnosed, and sets a time-phase separated by the end distance from the characteristic time-phase of the electrocardiographic waveform obtained from the subject to be diagnosed as the ending initial time-phase of the Doppler waveform to be diagnosed. Although the timing at which the characteristic time-phase of the electrocardiographic waveform appears (for example, a time-phase of an R-wave) varies for each subject to be diagnosed, it is possible to set the beginning initial time-phase and the ending initial time-phase suitable for the subject to be diagnosed by using the characteristic time-phase of the electrocardiographic waveform obtained from the subject to be diagnosed.

Further, it is desirable that, for example, the learned data is stored in the storage unit and includes feature amount data corresponding to the beginning time-phase and feature amount data corresponding to the ending time-phase obtained from the Doppler waveform information for learning by machine learning processing, the search unit searches for the beginning time-phase of the Doppler waveform based on a correlation between feature amount data obtained from the Doppler waveform near the beginning initial time-phase and the feature amount data corresponding to the beginning time-phase, and searches for the ending time-phase of the Doppler waveform based on a correlation between feature amount data obtained from the Doppler waveform near the ending initial time-phase and the feature amount data corresponding to the ending time-phase. Thus, in the search of the beginning time-phase and the ending time-phase of the Doppler waveform, the search based on the feature amount data obtained by the machine learning processing is implemented.

In addition, for example, it is desirable that the learned data is stored in the storage unit for each measurement item in a plurality of measurement items that use the Doppler waveform. Accordingly, it is possible to search for the beginning time-phase and the ending time-phase suitable for the measurement item based on the learned data stored for each measurement item. It is desirable that learned data corresponding to several measurement items that are similar to each other are aggregated and stored in the storage unit.

Advantageous Effect

According to the invention, there is provided an improved technique for searching for a beginning time-phase and an ending time-phase of a Doppler waveform. For example, according to a preferred aspect of the invention, in search of the beginning time-phase and the ending time-phase of the Doppler waveform, it is possible to search for a range that is defined near a beginning initial time-phase and an ending initial time-phase.

BRIEF DESCRIPTION OF DRAWINGS

FIG. 1 is a diagram illustrating a specific example of an ultrasound diagnosis device suitable for implementation of the invention.

FIG. 2 is a diagram illustrating a specific example of a display image used when generating a Doppler waveform.

FIG. 3 is a flowchart illustrating a specific example of a measurement time-phase setting processing of the Doppler waveform.

FIG. 4 is a diagram illustrating a specific example of initial time-phase data included in learned data.

FIG. 5 is a diagram illustrating a specific example of the search of the measurement time-phase.

FIG. 6 is a diagram illustrating a specific example of aggregation of the learned data.

DESCRIPTION OF EMBODIMENTS

FIG. 1 is a diagram illustrating a specific example of an ultrasound diagnosis device suitable for implementation of the invention. A probe 10 is an ultrasonic probe that transmits and receives ultrasonic waves, and scans a diagnosis region of a subject (living body) with an ultrasonic beam. Although a suitable specific example of the probe 10 is a sector probe or a linear probe, the probe 10 having a different scanning mode may also be used, and the probe 10 that stereoscopically scans the diagnosis region with an ultrasonic beam may also be used.

A transmission and reception unit 12 has a function of a transmission beam former and forms a transmission beam by outputting a transmission signal to a plurality of vibration elements included in the probe 10 and controlling transmission of the probe 10. In addition, the transmission and reception unit 12 has a function of a reception beam former, which forms a reception beam by performing phasing addition processing and the like on a plurality of signals obtained from the plurality of vibration elements, and obtains a reception signal along a reception beam.

A tomographic image formation unit 20 forms image data of a B-mode image (tomographic image) of the diagnosis region based on the reception signal obtained from the diagnosis region. In the formation of a tomographic image, the transmission and reception unit 12 scans the diagnosis area with an ultrasonic beam (a transmission beam and a reception beam corresponding to the transmission beam), and image data of a B-mode image corresponding to a scan plane is formed based on a reception signal obtained from the scan plane.

A Doppler waveform generation unit 30 obtains Doppler information from the reception signal collected from the diagnosis region and generates a Doppler waveform. The Doppler waveform generation unit 30 measures a Doppler shift generated in a reception signal of an ultrasonic wave obtained from a moving body such as a blood flow by, for example, a known Doppler processing, and obtains Doppler data (Doppler component in the beam direction) in the ultrasound beam direction of the moving body such as a blood flow.

In the Doppler measurement, a Doppler measurement point is set in the diagnosis region in accordance with operation by a user such as a doctor or an examination technician. The Doppler waveform generation unit 30 performs orthogonal detection wave processing, autocorrelation processing, and the like on the reception signal obtained from each reception beam corresponding to the Doppler measurement point, and obtains Doppler information (for example, Doppler shift information) at the Doppler measurement point. Furthermore, the Doppler waveform generation unit 30 forms waveform data of a Doppler waveform based on the Doppler information obtained from the Doppler measurement point.

An initial time-phase setting unit 40 sets a beginning initial time-phase and an ending initial time-phase of the Doppler waveform. In the setting, an electrocardiographic waveform signal obtained from the subject using an electrocardiograph or the like and learned data stored in a learned data storage unit 60 are used.

A measurement time-phase search unit 50 searches for a beginning time-phase of the Doppler waveform near the beginning initial time-phase, and searches for an ending time-phase of the Doppler waveform near the ending initial time-phase. In the search process, the learned data stored in the learned data storage unit 60 is used.

A Doppler measurement processing unit 70 executes trace processing of the Doppler waveform in a period from the beginning time-phase to the ending time-phase searched by the measurement time-phase search unit 50. The Doppler measurement processing unit 70 forms a trace line of a Doppler waveform from the beginning time-phase to the ending time-phase by using, for example, a known tracing processing (such as a Doppler auto-trace disclosed in Patent Literatures 3 to 6). Further, the Doppler measurement processing unit 70 executes a measurement processing related to a Doppler diagnosis based on the Doppler waveform in which the trace line is formed. Accordingly, for example, various measurement values for Doppler diagnosis are obtained.

A display processing unit 80 forms a display image based on the image data of the B-mode image obtained from the tomographic image formation unit 20 and data of the Doppler waveform and the measurement value obtained from the Doppler measurement processing unit 70. The display image formed in the display processing unit 80 is displayed on a display unit 82.

The control unit 100 controls the whole ultrasound diagnosis device of FIG. 1. An instruction received from the user such as the doctor or the examination technician via an operation device 90 is also reflected in an overall control by the control unit 100.

In the configuration shown in FIG. 1, each of the transmission and reception unit 12, the tomographic image formation unit 20, the Doppler waveform generation unit 30, the initial time-phase setting unit 40, the measurement time-phase search unit 50, the Doppler measurement processing unit 70, and the display processing unit 80 may be implemented by using hardware such as an electric electronic circuit or a processor, and a device such as a memory may also be used as necessary for the implementation. In addition, at least a part of functions corresponding to the above units may also be implemented by a computer. That is, at least a part of the functions corresponding to the above units may be implemented by cooperation of hardware such as a CPU, a processor, and a memory and software (a program) that defines operation of the CPU and the processor. For example, at least a part of functions of the initial time-phase setting unit 40, the measurement time-phase search unit 50, and the Doppler measurement processing unit 70 may be implemented by the computer, and the computer may also function as an ultrasound diagnosis device (Doppler waveform processing device).

The learned data storage unit 60 can be implemented by a storage device such as a semiconductor memory or a hard disk drive. Specific examples of the display unit 82 include a liquid crystal display, an organic electroluminescence (EL) display, or the like. The operation device 90 can be implemented by at least one of a mouse, a keyboard, a trackball, a touch panel, other switches, and the like. Then, the control unit 100 can be implemented by, for example, cooperation of the hardware such as the CPU, the processor, and the memory and the software (program) that defines the operation of the CPU and the processor.

An overall configuration of the ultrasound diagnosis device of FIG. 1 is as described above. Next, functions related to Doppler measurement implemented by the ultrasound diagnosis device of FIG. 1 will be described below in detail. Reference numerals in FIG. 1 are used in the following description of the configuration (part) illustrated in FIG. 1.

FIG. 2 is a diagram illustrating a specific example of a display image used when generating a Doppler waveform. FIG. 2 illustrates a specific example of an display image 85 in which a B-mode image 86 and a Doppler waveform image 87 are disposed side by side and an electrocardiographic waveform image 88 is disposed under the Doppler waveform image 87.

There are a large number of measurement items for a diagnosis using the Doppler waveform. For example, a large arterial blood flow measurement includes a plurality of measurement items such as a left ventricular ejection blood flow measurement (LVOT), an aortic valve stenosis blood flow measurement (AS), and an aortic valve reverse blood flow measurement (AR). In addition, a mitral valve blood flow measurement includes a plurality of measurement items such as a left ventricular inflow blood flow measurement (TransM), a mitral valve stenosis blood flow measurement (MS), and a mitral valve reverse blood flow measurement (MR). In addition, a pulmonary arterial blood flow measurement includes a plurality of measurement items such as a right ventricular ejection blood flow measurement (RVOT), a pulmonary valve stenosis blood flow measurement (PS), and a pulmonary valve reverse blood flow measurement (PR). In addition, a tricuspid valve blood flow measurement includes a plurality of measurement items such as tricuspid valve narrow blood flow measurement (TS) and tricuspid valve reverse blood flow measurement (TR). Further, there is also a plurality of measurement items based on a pulsed tissue Doppler method (TDI-PW).

As described above, there are a large number of measurement items for the diagnosis using the Doppler waveform. The user such as the doctor or the examination engineer appropriately adjusts the position and the posture of the probe 10 so that a measurement cross section corresponding to a desired measurement item is displayed. Accordingly, the display image 85 including the B-mode image 86 corresponding to the desired measurement cross section is displayed on the display unit 82.

When the desired measurement cross section is found, the user operates, for example, the operation device 90 to set the Doppler measurement point in the B-mode image 86 (for example, still image display) showing the measurement cross section. For example, in response to the operation by the user, a sample gate SG for Doppler measurement is set in the B-mode image 86. Then, an orientation of an ultrasonic beam (transmission beam and reception beam) DB for Doppler measurement is determined so as to pass through the sample gate SG.

When the orientation of the ultrasonic beam DB for Doppler measurement and the position of the sample gate SG are set in this way, the Doppler waveform generation unit 30 forms waveform data of a Doppler waveform based on Doppler information (for example, Doppler shift information) obtained from the sample gate SG (Doppler measurement point) via the ultrasound beam DB. A specific example of an image based on the waveform data is the Doppler waveform image 87 in FIG. 2.

In the specific example shown in FIG. 2, a time-phase cursor ST corresponding to the beginning time-phase of the Doppler waveform and a time-phase cursor ET corresponding to the ending time-phase of the Doppler waveform are illustrated in the Doppler waveform image 87. Therefore, the processing related to setting of the measurement time-phase (the beginning time-phase and the ending time-phase) of the Doppler waveform will be described below.

FIG. 3 is a flowchart illustrating a specific example of the measurement time-phase setting processing of the Doppler waveform. First, a measurement item corresponding to a Doppler waveform to be processed is selected from a plurality of measurement items (S1). For example, the user such as the doctor or the examination technician operates the operation device 90 to designate the measurement item.

Learned data corresponding to the measurement item is selected when the measurement item is selected (S2). The learned data storage unit 60 stores learned data of each measurement item for a plurality of measurement items that use the Doppler waveform. The learned data corresponding to the measurement item designated by the user is selected from the learned data for the plurality of measurement items stored in the learned data storage unit 60.

Then, an initial time-phase is set in the Doppler waveform to be processed, that is, the Doppler waveform obtained from the subject to be diagnosed, using the learned data corresponding to the selected measurement item (S3). Further, a measurement time-phase is searched in the Doppler waveform (S4).

In this way, when the measurement time-phase of the Doppler waveform to be processed, that is, when a beginning time-phase and an ending time-phase of the Doppler waveform are determined, the trace processing of the Doppler waveform in a period from the beginning time-phase to the ending time-phase is executed by the Doppler measurement processing unit 70 (S5). Further, the measurement processing related to the Doppler diagnosis is performed based on the Doppler waveform on which a trace line is formed (S6). Accordingly, for example, various measurement values for Doppler diagnosis are obtained.

The learned data is obtained from a large number of teacher data. For example, a large number of Doppler waveform data accumulated for learning for each measurement item are used as teacher data. The beginning time-phase and the ending time-phase of the Doppler waveform are input to the Doppler waveform data as the teacher data by a specialist such as the doctor. Further, the Doppler waveform data as the teacher data is associated with data of an electrocardiographic waveform signal obtained from the subject when the Doppler waveform data is obtained, and a distance (time) between the beginning time-phase and the ending time-phase of the Doppler waveform designated by the user can be obtained from a time-phase of an R-wave that is a characteristic time-phase of the electrocardiographic waveform.

Then, for each measurement item, the learned data is derived based on a plurality of teacher data corresponding to the measurement item. The learned data includes initial time-phase data and image feature amount data.

FIG. 4 is a diagram illustrating a specific example of the initial time-phase data included in the learned data. The initial time-phase data illustrated in FIG. 4 includes distance data for calculating the beginning initial time-phase (start) and the ending initial time-phase (end) for each measurement item of a plurality of measurement items 1 to 10. A specific example of the distance data is a distance from a main R wave (the number of pixels) and a normalized distance from the main R wave.

The R wave is one of characteristic time-phases included in the electrocardiogram waveform (ECG), and one of two consecutive R waves obtained from the electrocardiogram waveform signal is set as the main wave and the other is set as a sub wave. For example, out of two successive R waves, the R wave closer to the Doppler waveform part (from the beginning time-phase to the ending time-phase) used for measurement is set as the main wave and the farther R wave is set as the sub wave. A main R wave and a sub R wave are defined in advance for each measurement item since the Doppler waveform part (from the beginning time-phase to the ending time-phase) used for measurement is different for each measurement item.

Further, for each measurement item and for each of the beginning initial time-phase (start) and the ending initial time-phase (end) of the Doppler waveform, the distance from the main R wave (the number of pixels) and the normalized distance from the main R wave are stored in the learned data storage unit 60 as the initial time-phase data. The normalized distance is a value obtained by dividing the distance (the number of pixels) from the main R wave by the distance from the main R wave to the sub R wave (the number of pixels).

The distance data constituting the initial time-phase data (the distance from the main R wave or the normalized distance) is statistically obtained from a large number of teacher data. For example, for each measurement item, an average value of a distance obtained from a plurality of teacher data corresponding to the measurement item (the distance from the main R wave or the normalized distance) is set as the distance data of the initial time-phase data.

The initial time-phase setting unit 40 sets the beginning initial time-phase and the ending initial time-phase of the Doppler waveform obtained from the subject based on the initial time-phase data stored in the learned data storage unit 60 and the electrocardiographic waveform signal obtained from the subject to be diagnosed.

For example, in the case of Doppler diagnosis related to the measurement item 1, the initial time-phase data of the measurement item 1 is selected, the beginning initial time-phase is set at a position where the distance (the number of pixels) from the main R wave of the electrocardiographic waveform signal obtained from the subject is −150, and the ending initial time-phase is set at a position where the distance (the number of pixels) from the same R wave is 50. The beginning initial time-phase and the ending initial time-phase may be set by multiplying an R-wave distance of the electrocardiographic waveform signal obtained from the subject (the number of pixels from the main R wave to the sub R wave) by the normalized distance obtained from the initial time-phase data and adding the multiplication result to the main R wave of the electrocardiographic waveform signal obtained from the subject.

When the beginning initial time-phase and the ending initial time-phase of the Doppler waveform are set by the initial time-phase setting unit 40, the measurement time-phase search unit 50 searches for the measurement time-phase (the beginning time-phase and the ending time-phase) of the Doppler waveform. The measurement time-phase search unit 50 searches for the beginning time-phase of the Doppler waveform near the beginning initial time-phase set in the Doppler waveform, and searches for the ending time-phase of the Doppler waveform near the ending initial time-phase set in the Doppler waveform.

FIG. 5 is a diagram illustrating a specific example of the search of the measurement time-phase. FIG. 5 illustrates a Doppler waveform DP obtained from the subject to be diagnosed. A beginning initial time-phase SP and an ending initial time-phase EP are set in the Doppler waveform DP by the initial time-phase setting unit 40.

The measurement time-phase search unit 50 sets a beginning time-phase detection ROI (a region of interest for beginning time-phase detection) with reference to the beginning initial time-phase SP, and moves the disclosed time-phase detection ROI in the time-phase direction (the time axis direction) to search for the beginning time-phase. For example, an initial position of the disclosed time-phase detection ROI is set such that the center position of the disclosed time-phase detection ROI is the position of the beginning initial time-phase SP, and the disclosed time-phase detection ROI is moved from the initial position in the positive direction (the + direction) and the negative direction (the − direction) of the time axis. A moving range (a search range) of the disclosed time-phase detection ROI is, for example, n pixels (N is a natural number) in the positive direction from the initial position and N pixels in the negative direction. Then, the beginning time-phase is searched based on the image feature amount data of the Doppler waveform obtained from the disclosed time-phase detection ROI at each movement position.

In addition, the measurement time-phase search unit 50 sets an ending time-phase detection ROI (a region of interest for ending time-phase detection) with reference to the ending initial time-phase EP, and moves the ending time-phase detection ROI in the time-phase direction (the time axis direction) to search for the ending time-phase. For example, an initial position of the ending time-phase detection ROI is set such that the center position of the ending time-phase detection ROI is the position of the ending initial time-phase EP, and the ending time-phase detection ROI is moved from the initial position in the positive direction (the + direction) and the negative direction (the − direction) of the time axis. A moving range (a search range) of the ending time-phase detection ROI is, for example, n pixels (N is a natural number) in the positive direction from the initial position and N pixels in the negative direction. Then, the ending time-phase is searched based on the image feature amount data of the Doppler waveform obtained from the ending time-phase detection ROI at each movement position.

In the search by the measurement time-phase search unit 50, the learned data stored in the learned data storage unit 60 is used. The learned data stored in the learned data storage unit 60 includes image feature amount data in addition to the initial time-phase data (see FIG. 4). The image feature amount data is also obtained from a large number of teacher data. For example, a large number of Doppler waveform data accumulated for learning for each measurement item are used as teacher data. Then, for each measurement item, the image feature amount data corresponding to the beginning time-phase set by the user in the Doppler waveform as the teacher data and the image feature amount data corresponding to the ending time-phase set by the user in the Doppler waveform are derived from the plurality of teacher data corresponding to the measurement item by machine learning processing such as Adaboost, Random Forest and Deep Learning. The derived data is stored in the learned data storage unit 60.

The measurement time-phase search unit 50 searches for the beginning time-phase and the ending time-phase of the Doppler waveform DP based on the correlation between the image feature amount data stored in the learned data storage unit 60 and the image feature amount data obtained from the time-phase detection ROI set in the Doppler waveform DP of the subject to be diagnosed.

For each measurement item of a plurality of measurement items, image feature amount data corresponding to the beginning time-phase and image feature amount data corresponding to the ending time-phase are stored in the learned data storage unit 60. The measurement time-phase search unit 50 selects the image feature amount data corresponding to the measurement item of the Doppler waveform DP.

For example, the measurement time-phase search unit 50 compares the image feature amount data obtained from the beginning time-phase detection ROI with the image feature amount data (learned data) corresponding to the beginning time-phase, and searches for an optimal position (a time-phase) of the beginning time-phase detection ROI. For example, the position (the time-phase) of the beginning time-phase detection ROI at which the similarity of the image feature amount data is maximum is searched within the search range, and the position (the time-phase) is set as the optimal position (the time-phase) of the beginning time-phase detection ROI.

Further, the time-phase corresponding to the optimal position of the beginning time-phase detection ROI is set as the beginning time-phase of the Doppler waveform DP. For example, if the center position of the beginning time-phase detection ROI at the initial position is the position of the beginning initial time-phase SP, the center position of the beginning time-phase detection ROI at the optimum position is set as the beginning time-phase of the Doppler waveform DP.

In addition, for example, the measurement time-phase search unit 50 compares the image feature amount data obtained from the ending time-phase detection ROI with the image feature amount data (learned data) corresponding to the ending time-phase, and searches for an optimal position (a time-phase) of the ending time-phase detection ROI. For example, the position (the time-phase) of the ending time-phase detection ROI at which the similarity of the image feature amount data is maximum is searched within the search range, and the position (the time-phase) is set as the optimal position (the time-phase) of the ending time-phase detection ROI.

Further, the time-phase corresponding to the optimal position of the ending time-phase detection ROI is set as the ending time-phase of the Doppler waveform DP. For example, if the center position of the ending time-phase detection ROI at the initial position is the position of the ending initial time-phase EP, the center position of the ending time-phase detection ROI at the optimum position is set as the ending time-phase of the Doppler waveform DP.

Although the learned data is stored for each measurement item of the plurality of measurement items, the learned data corresponding to several measurement items similar to each other may be collected and stored in the learned data storage unit 60.

FIG. 6 is a diagram illustrating a specific example of aggregation of the learned data. FIG. 6 illustrates a specific example of the learned data stored in the learned data storage unit 60 before and after aggregation.

The learned data corresponding to each measurement item is stored in the learned data storage unit 60 before the aggregation for each measurement item of measurement items 1 to 12. On the contrary, learned data corresponding to several measurement items similar to each other are aggregated and stored in the learned data storage unit 60 after the aggregation. For example, the learned data of the measurement item 2 and the measurement item 3 are aggregated, and the aggregated learned data is used for both items of the measurement item 2 and the measurement item 3.

For example, the aggregated learned data corresponding to both items of the measurement item 2 and the measurement item 3 is obtained by using a plurality of teacher data corresponding to the measurement item 2 and a plurality of teacher data corresponding to the measurement item 3. Accordingly, for example, even when the number of the plurality of teacher data corresponding respectively to the measurement item 2 and the measurement item 3 is small, it is possible to obtain the aggregated learned data corresponding to both items by adding the plurality of teacher data corresponding to the measurement item 2 and the plurality of teacher data corresponding to the measurement item 3. For example, when there is a variation in the number of data of the teacher data for each measurement item, the variation in the number of data of the teacher data can be reduced by the aggregation. In addition, the capacity of the learned data stored in the learned data storage unit 60 can also be reduced by the aggregation.

In the specific example shown in FIG. 6, for example, the measurement item 4 and the measurement item 5, the measurement item 6 and the measurement item 7, the measurement item 8 and the measurement item 9, the measurement item 10 and the measurement item 11 are also aggregated as measurement items similar to each other. Specific examples of measurement items having a similarity suitable for the aggregation, that is, specific examples of measurement items whose Doppler waveform are similar to each other include a combination of left ventricular ejection blood flow measurement (LVOT) and right ventricular ejection blood flow measurement (RVOT), a combination of mitral valve stenosis blood flow measurement (MS) and tricuspid valve narrow blood flow measurement (TS), a combination of mitral valve reverse blood flow measurement (MR) and tricuspid valve reverse blood flow measurement (TR) combination, a combination of aortic valve stenosis blood flow measurement (AS) and pulmonary valve stenosis blood flow measurement (PS), and a combination of aortic valve reverse blood flow measurement (AR) and pulmonary valve reverse blood flow measurement (PR).

Although a preferred embodiment of the invention has been described above, the above-described embodiment is merely an example in all respects and does not limit the scope of the invention. The invention includes various modifications without departing from the spirit thereof.

REFERENCE SIGN LIST 10 probe
12 transmission and reception unit
20 tomographic image formation unit 30 Doppler waveform generation unit
40 initial time-phase setting unit
50 measurement time-phase search unit
60 learned data storage unit
70 Doppler measurement processing unit
80 display processing unit
90 operation device
100 control unit

The invention claimed is:

1. An ultrasound diagnosis device comprising:
at least one computer configured to:
generate a Doppler waveform based on reception data obtained by transmitting and receiving ultrasonic waves to and from a subject to be diagnosed;
obtain and store learned data including initial time-phase information obtained from Doppler waveform information;
set a beginning initial time-phase and an ending initial time-phase of the Doppler waveform based on the initial time-phase information;
search for a beginning time-phase of the Doppler waveform corresponding to the beginning initial time-phase, and search for an ending time-phase of the Doppler waveform corresponding to the ending initial time-phase;
store, as the initial time-phase information, a start time separation corresponding to time from a characteristic time-phase of an electrocardiographic waveform of the subject to the beginning initial time-phase, and store a time separation corresponding to time from the characteristic time-phase of the electrocardiographic waveform to the ending initial time-phase;
set a time-phase separated by the start time separation from the characteristic time-phase of the electrocardiographic waveform obtained from the subject as the beginning initial time-phase of the Doppler waveform of the subject, and set a time-phase separated by the end time separation from the characteristic time-phase of the electrocardiographic waveform obtained from the subject as the ending initial time-phase of the Doppler waveform of the subject;
wherein the learned data is stored in the at least one computer and includes feature amount data corresponding to the beginning time-phase and feature amount data corresponding to the ending time-phase obtained from the Doppler waveform information, which is machine learning processed by the at least one computer;
search for the beginning time-phase of the Doppler waveform based on a correlation between feature amount data obtained from the Doppler waveform corresponding to the beginning initial time-phase and the feature amount data corresponding to the beginning time-phase, and search for the ending time-phase of the Doppler waveform based on a correlation between feature amount data obtained from the Doppler waveform corresponding to the ending initial time-phase and the feature amount data corresponding to the ending time-phase;
determine the time separation from a main R wave of the electrocardiographic waveform;
move a beginning time-phase region of interest in a time-phase direction to search for the beginning time-phase; and
set the beginning time-phase to an optimal position of the region of interest.

2. The ultrasound diagnosis device according to claim 1, wherein
the learned data is stored in the at least one computer for each measurement item in a plurality of measurement items that use the Doppler waveform, each measurement item corresponding to a physical parameter of the subject, the at least one computer configured to obtain the learned data accumulated from Doppler waveform data for each measurement item.

3. The ultrasound diagnosis device according to claim 2, wherein
the learned data corresponding to several measurement items is aggregated and stored in the at least one computer.

* * * * *